United States Patent [19]

Anderson

[11] Plant 4,080

[45] July 19, 1977

[54] APRICOT TREE

[75] Inventor: Frederic W. Anderson, Merced, Calif.

[73] Assignee: Stark Bro's Nurseries and Orchards Co., Louisiana, Mo.

[21] Appl. No.: 721,541

[22] Filed: Sept. 8, 1976

[51] Int. Cl.[2] ..... A01H 5/03

[52] U.S. Cl. ..... Plt./39

[58] Field of Search ..... Plt./39

*Primary Examiner*—Robert E. Bagwill

*Attorney, Agent, or Firm*—Roger B. Webster

[57] ABSTRACT

An apricot tree which is large, vigorous, spreading, with a trunk and branches of medium size and medium texture, foliated with medium size, medium thick, cordate, abruptly pointed leaves having a glandular, coarsely serrate margin, flowering from small, medium length conic buds with medium size flowers, which have white petals and reddish sepals, in bloom two to three days after the Tilton (unpatented), and a regular and very productive bearer of small, uniform, symmetrical, oblong, freestone fruit having yellow skin and yellow flesh.

1 Drawing Figure

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of apricot tree resulted from my endeavors in the conduct of such plant breeding program.

ORIGIN OF THE VARIETY

The present variety of apricot tree was originated by me, in my experimental nursery and orchard located as aforesaid, as follows: The seed parent of the present variety was an unnamed, self-sterile variety that was selected by me from a group of seedlings grown from seeds of unknown varietal origin, obtained by me from Iran. The present variety is an open-pollinated seedling of such seed parent.

The variety, as thus originated, and under careful and continuing observation, evidenced — upon bearing fruit — certain novel characteristics which were commercially desirable, and I, therefore, undertook asexual reproduction of the variety preparatory to introducing it to the trade.

ASEXUAL REPRODUCTION OF THE VARIETY

Subsequent to origination and selection by me of the present variety of apricot tree, in the manner above described, I asexually reproduced it by top-working on mature trees in my said experimental orchard, and — in maturity — such reproductions ran true to the original tree in all respects.

SUMMARY OF THE VARIETY

The herein claimed variety of apricot tree is large, vigorous, spreading, with a trunk and branches of medium size and medium texture, foliated with medium size, medium thick, cordate, abruptly pointed leaves having a glandular, coarsely serrate margin, flowering from small, medium length conic buds with medium size flowers, which have white petals and reddish sepals, in bloom two to three days after the Tilton, and a regular and very productive bearer of small, uniform, symmetrical, oblong, freestone fruit having yellow skin and yellow flesh; the variety being particularly characterized by fruit having juice with a very high sugar content, and by a stone having a sweet kernel suitable for marketing.

BRIEF DESCRIPTION OF THE DRAWING

The drawing is an illustration, by photographic reproduction in color, of leaves and fruit of the variety; one of the fruit being cut into halves to expose the flesh, with the stone remaining in one such half.

DESCRIPTION OF THE VARIETY

The botanical details of this new and distinct variety of apricot tree — with color definitions (except those in common color terms) referenced to Maerz and Paul Dictionary of Color — are as follows:

Tree:
- *Size.*—Large.
- *Vigor.*—Vigorous.
- *Growth.*—Spreading.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.

Leaves:
- *Size.*—Medium; average length — 3"; average width — $2\frac{7}{8}$".
- *Form.*—Cordate; abruptly pointed.
- *Thickness.*—Medium.
- *Margin.*—Coarsely serrate.
- *Petiole.*—Medium length — average $1\frac{1}{2}$"; medium thickness.
- *Glands.*—Number and position — 3 to 6 on petiole; alternate; small; globose.
- *Color.*—Top side — Medium green (23-L-9); under side — Lighter green (22-J-7).

Flower buds:
- *Size.*—Small.
- *Length.*—Medium.
- *Form.*—Conic.

Flowers:

*Blooming period.*—Usually 2 to 3 days after Tilton.

*Size.*—Medium.

*Color.*—White petals, reddish sepals.

Fruit:

*Maturity when described.*—Eating ripe.

*Date of first picking.*—July 10th, 1976.

*Date of last picking.*—July 20th, 1976.

*Size.*—Small; uniform; average diameter axially — 1⅜"; average transversely in suture plane — 1½".

*Form.*—Uniform; symmetrical; oblong; compressed laterally.

*Suture.*—Distinct to shallow; extends from base to apex.

*Cavity.*—Rounded; elongated in suture plane, with suture showing on one side; average depth — 3/16".

*Apex.*—Depressed.

*Pistil Point.*—Wanting.

Skin:

*Thickness.*—Medium.

*Texture.*—Medium.

*Tenacity.*—Tenacious to flesh.

*Tendency to crack.*—None noted.

*Color.*—Apricot yellow (10-K-6) shading darker to 10-L-9.

Flesh:

*Juice.*—Abundant — rich; high sugar content; soluble solids — 26 to 28 Brix.

*Texture.*—Firm; crisp; meaty.

*Fibers.*—Few.

*Ripens.*—Evenly.

*Flavor.*—Subacid; delicate.

*Aroma.*—Wanting.

*Eating quality.*—Good.

*Color.*—Apricot yellow (10-L-7).

*Surface of pit cavity.*—Yellow.

Stone:

*Type.*—Free; parts from flesh smoothly.

*Size.*—Medium to small; average length — 1"; average breadth — ⅝"; average thickness — ½".

*Form.*—Oblong.

*Base.*—Straight.

*Apex.*—Rounded.

*Sides.*—Equal.

*Ventral edge.*—Thick.

*Dorsal edge.*—Full, without groove.

*Tendency to split.*—Slight.

*Kernel.*—Sweet.

*Color.*—Brown (8-H-10).

Use: Market — local. Canning. Drying.

Keeping quality: Good.

Resistance to insects and diseases: No unusual susceptibilities noted.

Shipping quality: Good.

The apricot tree and its fruit herein described may vary in slight detail due to climatic and soil conditions under which the variety may be grown; the present description being of the variety as grown in the Central Valley of California.

I claim:

1. A new and distinct variety of apricot tree, substantially as illustrated and described, which is large, vigorous, spreading, with a trunk and branches of medium size and medium texture, foliated with medium size, medium thick, cordate, abruptly pointed leaves having a glandular, coarsely serrate margin, flowering from small, medium length conic buds with medium size flowers, which have white petals and reddish sepals, in bloom two to three days after the Tilton, and a regular and very productive bearer of small, uniform, symmetrical, oblong, freestone fruit having yellow skin and yellow flesh; the variety being particularly characterized by fruit having juice with a very high sugar content, and by a stone having a sweet kernel.

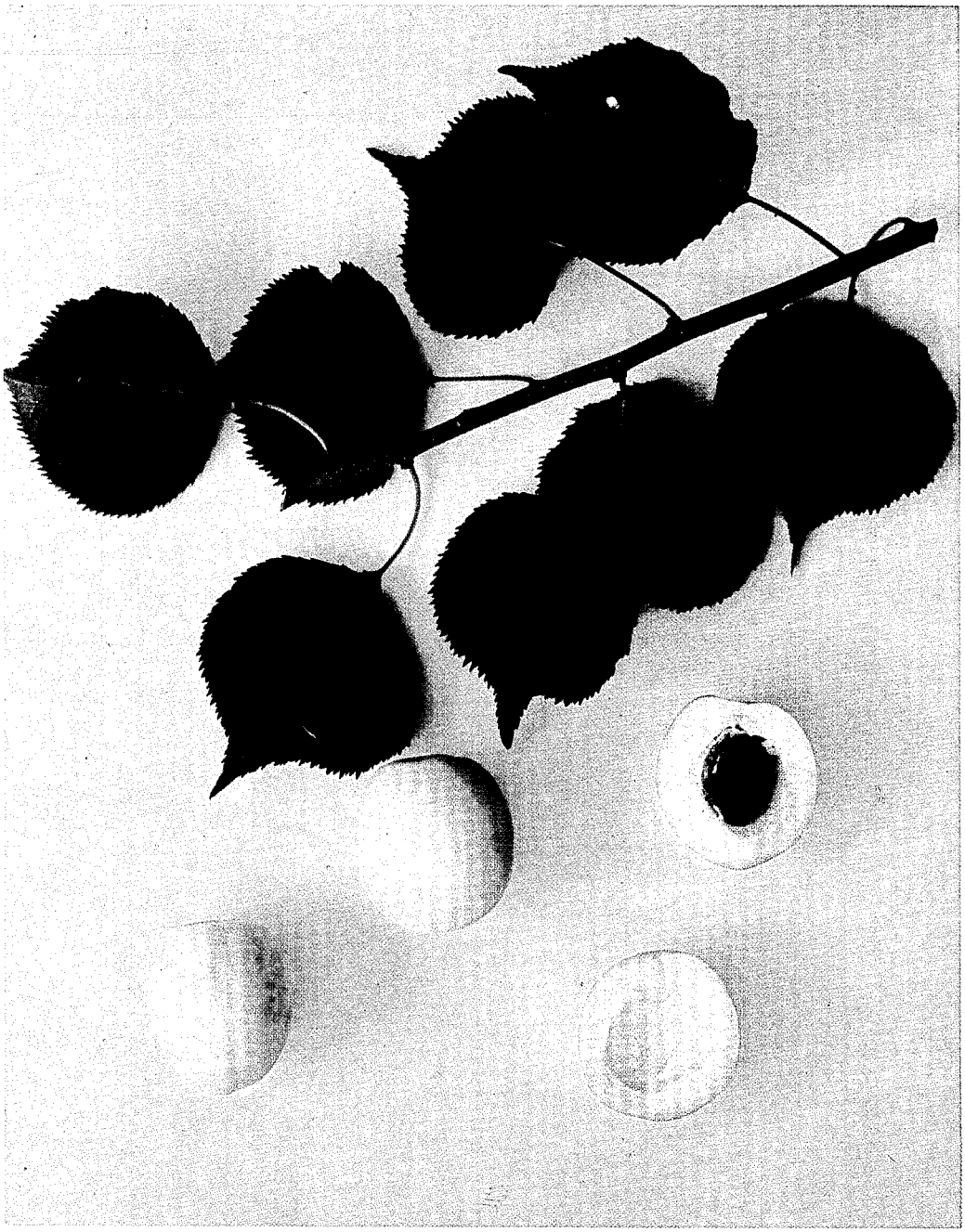

* * * * *